United States Patent [19]
Richer

[11] Patent Number: 5,628,797
[45] Date of Patent: May 13, 1997

[54] COSMETIC ANTERIOR CHAMBER, INTRAOCULAR LENS AND IMPLANTATION METHOD

[76] Inventor: Homer E. Richer, 2955 Central Blvd., Brownsville, Tex. 78520

[21] Appl. No.: 604,802

[22] Filed: Feb. 23, 1996

[51] Int. Cl.$^6$ .................................................. A61F 2/16
[52] U.S. Cl. ......................................................... 623/6
[58] Field of Search ........................................... 623/6

[56] References Cited

U.S. PATENT DOCUMENTS

| | | | |
|---|---|---|---|
| 4,605,409 | 8/1986 | Kelman | 623/6 |
| 4,636,210 | 1/1987 | Hoffer | 623/6 |
| 4,693,716 | 9/1987 | Mackool | 623/6 |
| 4,808,181 | 2/1989 | Kelman | 623/6 |

OTHER PUBLICATIONS

Robert L. Samper, et al—Intraocular Lenses Basics & Applications, San Francisco: Palace Press/American Academy of Opthamology (1993) pp. 29–34.

Clinical Applications of Optical Principles pp. 3648–3662.

*Primary Examiner*—Mary Beth Jones
*Attorney, Agent, or Firm*—J. Nevin Shaffer, Jr.; Shaffer & Culbertson

[57] ABSTRACT

An anterior chamber intraocular lens implant which is donut-shaped and lacks refractive power in the portion covering the pupil of the eye. The lens includes a circular joint, or hinge, and locking latch for pivoting the two members forming the implant from a first, open position to a second, closed position. Additionally, minute, soft circular haptics are provided for keeping the lens flexible and in position and which allow only those spots to touch the angle structures of the eye. This lens is made of several basic colors that will give the appearance of a different color to an individuals iris.

7 Claims, 1 Drawing Sheet

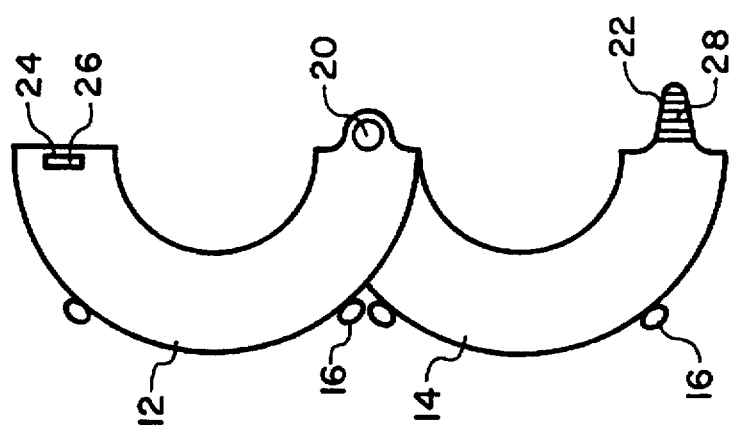
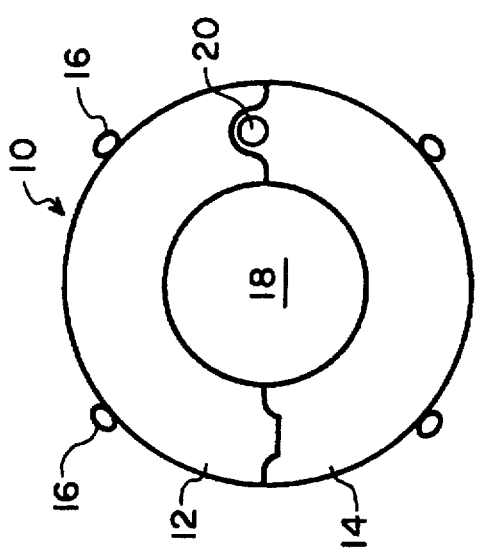
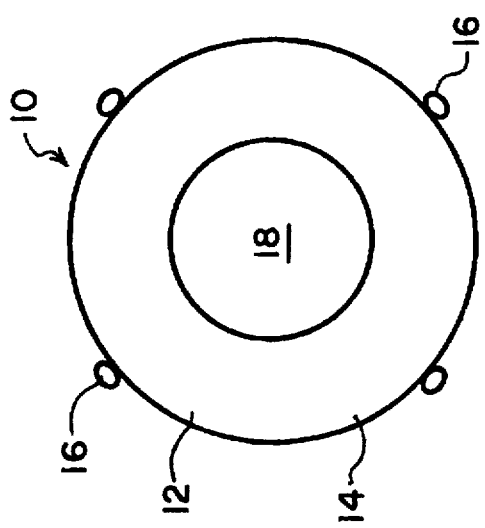
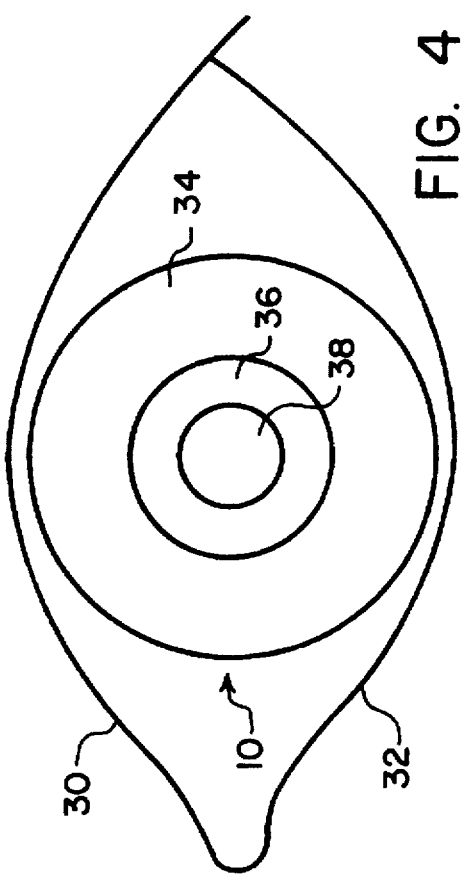

COSMETIC ANTERIOR CHAMBER, INTRAOCULAR LENS AND IMPLANTATION METHOD

BACKGROUND OF THE INVENTION

This invention relates to an intraocular lens for implantation in the anterior chamber of the eye. The lens is primarily intended for use in cosmetic applications but has other uses as will be developed.

At one time, anterior chamber intraocular lenses were the most commonly used intraocular lens in the United States because they colaid be used with intracapsular cataract extraction. However, such lenses were characterize, by a number of disadvantages and limitations (characterized at Pages 29–34 of R. L. Stamper et al., Intraocular Lenses: Basics and Clinical Applications, San Francisco: Palace Press/American Academy of Ophthalomogy (1993), which pages are incorporated herein in their entirety by this specific reference thereto) which, along with a shift to extracapsular cataract extraction, have limited their use to situations in which a posterior chamber lens cannot be used. Such lenses are, however, relatively easy to implant either in intra- or extracapsular surgery. They preserve normal pupillary function, and they also may be used in conjunction with other procedures such that they do represent an attractive alternative to the posterior chamber lens if some of these referenced disadvantages can be overcome. Further, the ease of implantation suggests possible additional uses for such lenses, primarily, their use for cosmetic purposes.

One disadvantage of the anterior chamber lens is the need for a lens which is sized correctly for a particular eye. Accurate preoperative prediction of lens size is problematical and a large lens pressures the chamber angle and corneoscleral wound, producing necrosis, tenderness, and possible wound disruption. An implant which is too small may produce iritis, iris atrophy and other contraindications as summarized in the above incorporated reference. Although the present invention is not so limited in its scope, by providing a solution to these size-induced problems, the intraocular lens of the present invention makes the use of this lens possible in, for instance, cosmetic applications.

SHORT STATEMENT OF THE INVENTION

In more detail, the intraocular lens of the present invention solves these problems by providing a lens comprised of first and second members which are preferably, but not necessarily, "C"-shaped, and which are therefore referred to as being semicircular in nature, and which are movably connected to each other for movement from a first, open position to a second, closed position. The first, open position facilitates implantation into the anterior chamber of the eye; in a second, closed position, the first and second semicircular members form a substantially circular optic. The first and second semicircular members are provided with a retaining mechanism for retaining the optic formed by the first an second semicircular members in the second, closed, position and a plurality of haptics for supporting the optic in the anterior chamber. In a particularly preferred embodiment, the retaining mechanism is a latch comprised of a tail extending from the first semicircular member and a tab on the second semicircular member for engaging the tail to retain the first and second members in the second, closed, position and either the tail is provided with a plurality of detentes spaced along the length of the tail or a plurality of spaced tabs are provided on the second member so that the diameter of the substantially circular optic is capable of being varied to fit the anterior chamber of the eye.

BRIEF DESCRIPTION OF THE DRAWINGS

Other objects, advantages, and features of the present invention will become more fully apparent from the following detailed description of the preferred embodiment, the appended claims and the accompanying drawings in which:

FIG. 1 is a plan view of the anterior surface of a preferred embodiment of the intraocular lens of the present invention as constructed for use as a cosmetic lens;

FIG. 2 is a plan view of the posterior surface of the lens in FIG. 1;

FIG. 3 is a plan view of the anterior surface of the lens of FIG. 1; and

FIG. 4 is a schematic representation of a human eye having the lens of FIG. 1 implanted in the anterior chamber thereof.

DETAILED DESCRIPTION OF THE PREFERRED EMBODIMENT

The preferred embodiment of the present invention is illustrated by way of example in FIGS. 1–4. However, those skilled in the art will recognize from this description that the invention is not limited in its scope to the cosmetic lens shown in those figures.

Referring now to FIGS. 1 and 2, there is shown an intraocular lens constructed in accordance with the present invention which is intended for use as a cosmetic lens. The lens is comprised of a substantially circular optic 10 formed of first and second semi-circular members 12 and 14, respectively, having a plurality of haptics 16 formed or integrally attached around the periphery thereof for supporting the optic 10 in the anterior chamber of the eye. Although shown in the figures as being "C"-shaped, it will be recognized by those skilled in the art who have the benefit of this disclosure that the first and second members 12 and 14 are shaped in this configuration because of the intended use of the lens for cosmetic purposes; specifically, the material comprising each of the first and second members 12 and 14 is colored so as to change the color of the iris (not shown in FIGS. 1 and 2) of the eye. So as not to interfere with vision and/or color perception, however, the center portion 18 of the optic 10 is transparent or, in the preferred embodiment shown, the optic 10 is not continuous over, and does not cover, the entire iris, being donut or ring-shaped. Nevertheless, the first and second members are referred to herein as being semi-circular in contemplation of members which are "D"-shaped (or half circles) or formed in other shapes such as would be utilized in an optic which, for instance, varies to some degree from the circular optic shown to a slightly ovoid or elliptically-shaped optic.

Each of the first and second members 12 and 14 is molded from a suitable material such as a plastic like polymethylacrylate (PMMA) so as to be semi-flexible in nature. In the preferred embodiment shown, the PMMA is itself colored or a thin layer of colored material is sandwiched between two thin layers of PMMA. Because there is no outward difference in the appearance of an optic of either construction, the attached figures are considered illustrative of both constructions. As known in the art, the semicircular members are molded in a shape so that the optic is slightly concave so as to provide a vault that clears the iris of the eye into which it is implanted.

The optic 10 is provided with a moveable connection, such as hinge 20, molded into the first and second semicircular members 12 and 14. Because of the "C"-shaped configuration of first and second members 12 and 14, the hinge 20 is located relatively near the periphery of the optic 10, but this location is preferred even in the case of first and second members which are shaped in other configurations so as to facilitate implantation of the lens as more fully described below. Hinge 20 allows the pivoting of the first and second members 12 and 14 from a first, open, position, as shown in FIG. 3, to a second, closed, position forming the optic 10 as best shown in FIG. 2.

One of the first and/or second members 12 and 14 is provided, with a tail 22 and the other with a complementary tab 24 for engaging tail 22 to form a retaining mechanism for retaining the first and second members 12 and 14 in the second, closed position. In the embodiment shown, the tab 24 is formed in one surface with a slot 26 through which the tail 22 is received, the combination of the sizes of the slot 26 and tail 22, as well as the semi-rigid nature of the PMMA comprising the first and second members 12 and 14, providing sufficient friction between the tab/surface 24 and the tail 22 to insure that the first and second members are retained in the second, closed position. Again, because of the "C"-shaped configuration of the first and second members 12 and 14, the tail 22 is advantageously formed on the end of the member opposite the hinge 20, but those skilled in the art will recognize that the latch need not necessarily be located in a position 180 degrees around the periphery of optic 10 from hinge 20.

As best shown in FIG. 3, the tail 22 is provided with a plurality of detentes, or serrations, 28 for engagement by the tab 24. This construction allows the insertion of a tail 22 through the slot 26 in a manner which provides a range of variation in the diameter of the optic 10 depending upon the extent to which the tail 22 extends through slot 26, while providing positive retention of the tail 22 by tab 24 at each diameter so as to maintain the first and second members in the second, closed position at a chosen diameter. In an alternative embodiment (not shown), the tail is provided with an enlarged end and, instead of a single slot such as the slot 26, a plurality of spaced slots are provided so that the enlarged end of the tail will be retained within any of the slots so as to select the desired diameter of the optic.

Referring now to FIG. 4, there is shown a schematic representation of the lens of the present invention after implantation in the anterior chamber of the eye. The upper and lower lids are represented at reference numerals 30 and 32, respectively, and the cornea is shown at reference numeral 34. The optic 10 covers a large portion of the iris 36, but the central portion of optic 10 (the portion labelled with reference numeral 18 in FIGS. 1 and 2) leaves the pupil 38 and a portion of the iris 36 uncovered. The diameter of the uncovered portion is such that the pupil 38 is able to dilate to as much as 5-6 mm without being obstructed by the first and second members 12 and 14.

In use, the intraocular lens of the present invention is implanted in the anterior chamber of the eye by the following, or some similar or equally effective, procedure. After obtaining adequate local anesthesia and akinesia, and following standard preoperative prepping procedures, a lid speculum is placed on the eye. A superior bridle suture is placed and standard superior limbal peritomy is performed. Wet cautery is used for hemostasis. A 5mm incision is made with a beaver blade to half scleral thickness, approximately 1-2mm from the limbus, and the incision is dissected to clear cornea. With a super blade, a paracentesis is made at the 3 o'clock limbus followed by penetration via the clear corneal incision superiorly into the anterior chamber. MIOCHOL™ intraocular (CooperVision) is instilled into the anterior chamber followed by VISCOAT to maintain the depth of the chamber. A SHEETS-GLIDE™ is placed over the pupil and the implant, in a closed-scissored configuration, is placed down into the anterior angle structures. The SHEETS-GLIDE™ is removed and the, lens haptics are opened. The latch is closed at the diameter selected for proper fit in the eye (white to white horizontal diameter) at approximately 12 o'clock. After assuring good placement and centration, the VISCOAT is removed and the wound is closed with a single suture,. The conjunctiva is brought over the wound and the eye is dressed with appropriate antibiotics and an eye patch.

Although shown in a single embodiment in the figures, it will be recognized from the description set out herein that the present invention contemplates lenses which, although not constructed exactly as shown in the figures, function in substantially similar fashion to achieve substantially similar results as the lens which is shown. It has been noted, for instance, lens may be folded instead of hinged and, if hinged, that the latch may be of more than one construction and that the optic may be formed of two semicircular, D-shaped members rather than C-shaped members. All such changes are intended to fall within the spirit and scope of the following claims. That is, while the present invention has been disclosed in connection with the preferred embodiment thereof, it should be understood that there may be other embodiments which fall within the spirit and scope of the invention as defined by the following claims.

I claim:

1. An intraocular implant for placement in the anterior chamber of the eye comprising:
   a) first and second semicircular members;
   b) movable connection means for connecting said first and second semicircular members to each other for pivoting from a first, open position for facilitating implantation into the anterior chamber of an eye to a second, closed position forming a substantially circular optic;
   c) a plurality of haptics formed integrally with said first and second semicircular members; and
   d) a retaining means for retaining said first and second semicircular members in said second, closed position after implantation in the anterior chamber.

2. The implant of claim 1 wherein said retaining means comprises a latch with a tail extending from said first semicircular member for engaging said tail to retain said first and second semicircular members in said second, closed position.

3. The implant of claim 2 wherein said tail is provided with a plurality of detents spaced along the length thereof for engagement with a tab of said second semicircular member when in said second, closed position.

4. The implant of claim 1 wherein each of said first and second members so that the optic formed when said first and second members are in said second, closed position is concave.

5. The implant of claim 1 wherein each of said first and second members is C-shaped.

6. The implant of claim 1 wherein said moveable connection means comprises a hinge.

7. A method for implantation of an intraocular implant comprising the steps of:
   a) preparing an eye to receive an intraocular implant;
   b) constructing said implant with:
      i) movable connection means for connecting first and second semicircular members to each other for pivoting from a first, open position for facilitating implantation into the anterior chamber of an eye to a second, closed position forming a substantially circular implant;

ii) a plurality of haptics formed integrally with said first and second semicircular members; and iii) a retaining means for retaining said first and second semicircular members in said second, closed position after implantation in the anterior chamber.

c) forming the intraocular implant in a closed-scissors configuration;

d) inserting the intraocular implant into the eye;

e) opening the intraocular implant;

f) selecting an appropriate diameter to suit the eye;

g) engaging the retaining means at the selected diameter;

h) securing the intraocular implant in place within the eye; and i) closing the eye where the intraocular implant was inserted.

* * * * *

UNITED STATES PATENT AND TRADEMARK OFFICE
CERTIFICATE OF CORRECTION

PATENT NO. : 5,628,797
DATED : May 13, 1997
INVENTOR(S) : Homer E. Richer It is certified that error appears in the above-identified patent and that said Letters Patent is hereby corrected as shown below:

In Column 1, Line 12, delete the word "colaid" and insert the word --could--.

In Column 1, Line 13, change "characterize" to --characterized--.

In Column 3, Line 10, delete the "," after the word "provided".

In Column 4, Line 24, delete the word "oiler" and insert the word --other--.

In Claim 4, Column 4, Line 50, delete the words "each of".

In Claim 4, Column 4, Line 51, delete the words "so that the optic"; change "formed" to "form" and insert after the word "form" --a concave shape--.

In Claim 4, Column 4, Lines 52 and 53, delete the words "is concave".

Signed and Sealed this

Twelfth Day of August, 1997

Attest:

BRUCE LEHMAN

Attesting Officer

Commissioner of Patents and Trademarks